United States Patent [19]

Smith

[11] Patent Number: 4,680,272

[45] Date of Patent: Jul. 14, 1987

[54] METHOD FOR DETECTING MOLECULES CONTAINING AMINE OR THIOL GROUPS

[75] Inventor: Tammy L. Smith, Los Angeles, Calif.

[73] Assignee: University of California, Berkeley, Calif.

[21] Appl. No.: 790,349

[22] Filed: Oct. 23, 1985

[51] Int. Cl.4 .................... G01N 21/77; G01N 33/52; G01N 33/68

[52] U.S. Cl. ...................... 436/86; 436/111; 436/120; 436/172

[58] Field of Search ............... 436/86, 87, 88, 111, 436/112, 120, 161, 162, 164, 169, 172, 174, 175, 176, 177; 250/459.1, 461.1, 461.2

[56] References Cited

U.S. PATENT DOCUMENTS

| | | | |
|---|---|---|---|
| 3,481,952 | 12/1969 | McConnell et al. | 436/87 X |
| 3,527,712 | 9/1970 | Renn et al. | 436/161 X |
| 3,876,881 | 4/1975 | Bohlen | 250/461.1 X |
| 3,891,670 | 6/1975 | Kanaoka et al. | 436/120 X |
| 4,135,816 | 1/1979 | Niemann et al. | 250/461.2 X |
| 4,222,836 | 9/1980 | Kerr et al. | 436/161 X |

FOREIGN PATENT DOCUMENTS 0031055  2/1985  Japan ..................... 436/161

OTHER PUBLICATIONS

Kanaoka et al., Biochim. Biophys. Acta, vol. 207, No. 2, pp. 269–277, 1970.

Augustin et al., Chemical Abstracts, vol. 92, Abstract No. 92:93863w, 1979.

Lynch et al., J. of Heterocyclic Chemistry, vol. 9, No. 5, pp. 1027–1032, 1972.

Switzer et al., Anal. Biochem., vol. 98, No. 1, pp. 231–237, 1979.

Oda et al., Tetrahedron, vol. 24, pp. 4051–4056, 1968.

Primary Examiner—Barry S. Richman
Assistant Examiner—Robert J. Hill, Jr.
Attorney, Agent, or Firm—Irell & Manella

[57] ABSTRACT

A stain for detecting molecules having amine or thiol groups, comprising halogenated maleimides and derivatives thereof, such as halogenated maleicdiamides. Upon binding to nitrogen- or sulfur-containing molecules, such as proteins, the halogenated stains undergo a chemical transformation which causes them to fluoresce. By applying the stain to a substrate suspected of containing amine or thiol groups and applying an ultraviolet light source thereto, any fluorescence, indicative of the presence of amines or thiols, can be readily detected.

15 Claims, 1 Drawing Figure

DICHLOROMALEIMIDE

DIBROMOMALEIMIDE

DICHLOROMALEICDIAMIDE

METHOD FOR DETECTING MOLECULES CONTAINING AMINE OR THIOL GROUPS

This invention was made with Government support under Grant No.: NIH 5-RO1-6M 2427 with the National Institutes of Health and the University of California. The Government has certain rights in this invention.

BACKGROUND OF THE INVENTION

This invention relates generallly to biochemical assays, and more specifically, to means for detecting protein.

The detection of proteins has important application in biochemistry, clinical chemistry and medicine. For example, determing the presence and quantity of proteins in urine or blood is diagnostically important and may be of crucial importance in evaluating an emergency protocol whee proteinuria is suspected, which may indicate such conditions as heart failure or the onset of renal disease. Moreover, in conventional biochemical assays such as electrophoresis and chromatography, which are used for separating organic molecules, the detection of general proteins is commonly required.

In order to visually detect the presence of protein, a multi-step process is presently necesssary using conventional techniques. A solution suspected of containing protein is placed on a substrate as to which any protein will attach or become engulfed. A stain which preferentially binds with protein is then applied to the substrate and allowed to react with any protein present. Unbound stain is removed and the substrate evaluated for stain, indicating the presence of protein.

Presently, the preferred stain for general protein is coomassie blue, or anazolene sodium. This stain has a sulfonate group which binds ionically to the positively charged amines of protein. The dye takes an average of six to twelve hours to stain, for example, a polyacrylamide electrophoretic gel. Such a lengthly time period significantly decreases the utility of the assay. Recently, a new stain based on the chemistry of nickel has been developed (Kodavue Electrophoresis Kit, Eastman Kodak Co., Rochester, N.Y.). While the time involved is significantly reduced, the assay requires a cumbersome number of fixing, washing and drying steps.

Because traditional stains are visible both before and after attachment to the proteins, standard protein assays cannot be used to detect protein in solution without first immobilizing the protein. The presence of protein is determined solely by the affinity of the stain for the protein relative to the washing solution.

It will therefore be appreciated that there exists a long standing need for a stain for protein which is fast, effiient and easy to use. Additionally, in order to allow use of the stain to detect protein which is free in solution, the dye should exhibit a visually detectable change upon binding to protein. The present invention satisfies these needs and provides related advantages as well.

SUMMARY OF THE INVENTION

The present invention involves halogenated maleimides and derivatives thereof such as maleicdiamides, which do not fluoresce in thr visible region, for use as stains for detecting the presence of protein or other molecules containing amine or thiol groups. As used hereinafter, the term "halogenated maleimide" shall include both halogenated maleimides themselves as well as the maleicdiamide derivatives. Preferably, the halogenated maleimide is dichloromaleimide or dibromomaleimide. Upon binding to nitrogen- or sulfur-containing molecules, such as proteins, such halogenated maleimides undergo a chemical transformation which causes them to fluoresce. By applying a composition of a halogenated maleimide to a substance suspected of containing protein and applying an ultraviolet light source thereto, any fluorescence, indicative of the presence of protein, can be readily detected. Such staining takes only about 15 minutes. The stain can be used to detect protein which is bound to a substrate as well as that in solution. These stains are thus fast and efficient to use and low in cost. Additionally, because they do not contain charged groups, they will not interfere with other chemical processes occurring in the media in which they are used. For example, if the protein has been labelled radioactively for other purposes, the stain of the present invention will not mask the emission.

In one aspect of the invention, a halogenated maleimide is added to a test tube containing a solution, such as a blood derivative or urine, suspected of containing protein. An ultraviolet light source is used to visualize any fluorescence, which indicates the presence of protein.

In another aspect of the invention, a halogenated maleimide is applied to a solid surface, such as an electrophoretic gel or chromatographic substrate, on which the components of a substance suspected of containing protein have been separated by appropriate means. Ultraviolet light is then applied in order to visualize the presence and location of any molecules containing amines or thiols.

It will be appreciated that the use of halogenated maleimides as stains for proteins constitutes an important improvement in the art of protein assays. Other features and advantages of the present invention will become apparent from the following more detailed description which illustrates, by way of example, the principles of the invention.

DETAILED DESCRIPTION OF THE PREFERRED EMBODIMENT

The present invention involves the use of halogenated maleimides to determine the presenceof proteins, or other molecules containing amine or thiol groups, in certain substances or solutions. The halogenated maleimide is contacted with the solution suspected of containing such molecules and allowed to react therewith. When bound to protein, the halogenated maleimides undergo a chemical transformation which results in fluorescence. Fluorescence can be broadly defined as the emission of light by atoms that have absorbed energy from some other light source. In the presence of ultraviolet light, the fluorescence is readily visible, allowing visual determination of the presence of protein. Further, the intensity of the fluorescence is roughly proportional to the quantity of amine of thiol groups present, thereby permitting quantitative determination as well.

Figure 1:
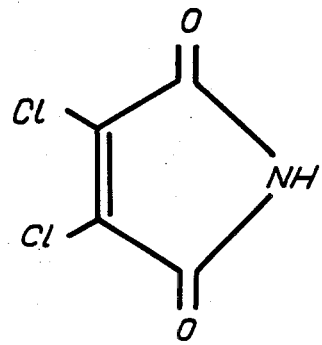
FIG. 1 presents the chemical structure of dichloromaleimide, dibromomaleimide and dichloromaleicdiamide.
Figure 1:
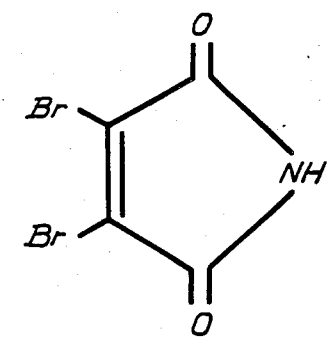
Figure 1:
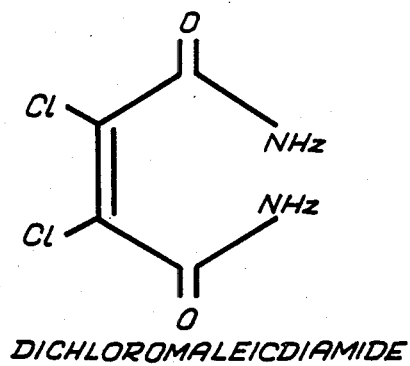

The halogenated maleimide of preference is dichloromaleimide, or $C_4NCl_2O_2H$. Other preferred forms are dibromomaleimide, $C_4NBr_2O_2H$ and dichloromaleicdiamide, $C_4N_2Cl_2O_2H_2$ and dibromomaleicdiamide $C_4N_2Br_2O_2H$. The structures of the first three of these compounds are presented in FIG. 1. Dibromomaleicdiamide has bromine groups substituted for the chlorine groups of dichloromaleic diamide. Other halogenated maleimides may also be used.

While not wishing to be bound by the explanation, it is believed that the fluorescence of the maleimide in the presence of protein results from a nucleophilic attack on the halogenated maleimide by the amino and thiol groups, and the subsequent elimination of the halogen. Since any halogen can serve as the leaving group, and all halogens have similar electron configurations, any halogenated maleimide/protein complex should fluoresce.

In accordance with the invention, a sample of material suspected of containing protein is placed in a transparent container and enough sodium dodecylsulfate added to achieve a final concentration of SDS of 10%. A halogenated maleimide in an organic solvent is added and the solution heated. Any fluorescence can be detected in the presence of ultraviolet light.

In accordance with a further aspect of the invention, solid substrates potentially having protein bound thereto are placed in a solution of organic solvents containing a halogenated maleimide. After several minutes incubation, fluorescence in the presence of ultraviolet light can be detected if protein is present.

EXAMPLE I

Synthesis of Dichloromaleimide

Dichloromalemide was synthesized according to the method of Degena et al., Brit. No. 1,145,583 (C.A.). A saturated solution of dichloromaleic anhydride (Aldrich Chemical Co., Inc., Milwaukee, Wis.) in ethylacetate was heated on a hotplate to boiling. This solution was filtered through activated charcoal and recrystallized by reheating the solution to boiling, adding cyclohexane, evaporting excess solvent and slowly cooling the solution causing purified dichloromaleic anhydride precipitates. Four grams (4.0 g.) of this purified dichloromaleic anhydride together with 1.5 g urea and 4.8 g sodium chloride were placed in a round bottom flask equipped with a reflux condenser, a stirring bar and a nitrogen line. The material was heated to 115° C. in an oil bath, stirring constantly. After evolution of carbon dioxide began, the flask was removed from the heat source. When the evolution of carbon dioxide subsided, 30 ml of water were added to the flask and the mixture heated to 100° C. for 10 minutes, cooled, filtered through Whatman Filter Paper #1 (Whatman Limited, England), and recrystallized from water. The yield from this procedure was about 55%. The melting point of the dichloromaleimide is 178.5° to 179° C.

EXAMPLE II

Preparation of Dbromomaleimied

Dibromomaleimide was synthesized according to the method of Plancher (Beilstein, System Number 3202 21:403).

One gram of maleimide (Aldrich Chemical Co., Inc., Milwaukee, Wis.), 5 ml of water and 1.8 g of bromine were placed in a round bottom 25 ml flask equipped with a reflux condenser, nitrogen line and stir bar. While stirring, a sun lamp (Westinghouse reflection infrared heat lamp 115-125 V, 250W Westinghouse Electric Corp., Pittsburgh, Pa.) was used to illuminate the flask for five minute periods with five minute intervals until the solution was white or off-white indicating that the bromine was consumed. The solution was cooled on ice and filtered. The solid product was recrystallized from water or acetonitrile. Alternatively, after illumination the solution can be extracted with carbon tetrachloride, the solvent evaporated and the product recrystallized. The procedure yielded 55% of recrystallized product having a melting point of 229° to 230° C.

EXAMPLE III

Detection of Proteins in Solution

Approximately 0.25 ml of solution suspected of containing protein was placed in a test tube and enough sodium dodecylsulfate added to make a 10% solution. About 0.75 ml of a dichloromaleimide/acetonitrile solution (2 mg/ml) and 1.0 ml dimethylsulfoxide were added and the resulting solution was heated in a water bath at 50° C. for 5-10 minutes. A hand held ultraviolet lamp (Mineralight Lamp, UltraViolet Products, Inc., San Gabriel, Calif.) was used to apply light of a wavelength of about 365 nm to the test tube. Where the initial solution contains a protein, a green-blue fluorescence appears in the solution. By comparison to a control solution consisting of a blank test tube or tube not containing protein, artifacts resulting from non-specific fluorescence can be eliminated. The intensity of the fluorescence is proportional to the number of amine or thiol groups present, permitting quantification by comparison to tubes containing standardized solutions.

EXAMPLE IV

Staining of Protein on Electrophoretic Gels

Electrophoretic techniques follow those described by Laemmli, Nature 227:680 (1970). Sample solutions suspected of containing proteins and a tracking dye, preferably bromophenol blue, were applied to acrylamide/SDS gels. The gels were exposed to an electrical current of 120 v using a tris (0.6 wt. %), glycine (2.88 wt. %), SDS (0.1 wt. %) buffer. After removal from the electrophoretic apparatus, the gels were soaked in an acetonitrile (70 vol. %) acetic acid (10 vol. %) water (20 vol. %) solution for ten minutes. The gel was then placed in a solution warmed to 45° C. of acetonitrile (50 vol. %), dimethylsulfoxide (5 vol. %), carbonate buffer (45% vol. %), pH 10.6, I=0.3, containing 18 mM dichloromaleimide. Preferably, the pH of the buffer is 8-11, and most preferably 10.6. Under ultraviolet light (Mineralight UltraViolet Products, Inc., San Gabriel, Calif.; wavelength=365 nm) a green fluorescence appears in any band containing protein. Indefinite storage in a solution of acetonitrile (50 vol. %) acetic acid (10 vol. %) water (40 vol. %) preserves the gels without affecting their capacity to fluoresce.

Although the invention has been described with reference to the presently-preferred embodiment, it should be understood that various modifications can be made by those skilled in the art without departing from the invention. Accordingly, the invention is limited only by the following claims.

I claim:

1. A method of analyzing a solution for the presence of molecules having amine or thiol groups, comprising the steps of:

(a) providing a sample of the solution;

(b) adding a halogenated maleimide to said sample to form a mixture;

(c) applying ultraviolet light to said mixture; and (d) monitoring said mixture for fluorescence, wherein any fluorescence in said mixture indicates the presence of molecules containing amine or thiol groups in the solution.

2. The method of claim 1, wherein said solution is a blood derivative.

3. The method of claim 1, wherein said solution is urine.

4. The method of claim 1, wherein said halogenated maleimide is dissolved in an organic solvent.

5. The method of claim 1, wherein said adding step further comprises the step of heating said mixture.

6. The method of claim 1, wherein the solution is analyzed for the presence of proteins as the molecules having amine or thiol groups.

7. A method of analyzing a composition for the presence of molecules having amine or thiol groups, comprising the steps of:

(a) placing a sample of the composition on a carrier;

(b) placing said carrier in a solution containing a halogenated maleimide, whereby said halogenated maleimide will selectively bind to any molecules containing amine or thiol groups which are present on said carrier;

(c) applying ultraviolet light to said carrier; and (d) monitoring said carrier for fluorescence, wherein any fluorescence in said carrier indicates the presence of molecules containing amine or thiol groups in the composition.

8. The method of claim 7, wherein said carrier is an electrophoretic gel.

9. The method of claim 7, wherein said carrier is a chromatographic substrate.

10. The method of claim 7, wherein said halogenated maleimide is dichloromaleimide.

11. The method of claim 7, wherein said halogenated maleimide is dibromomaleimide.

12. The method of claim 7, wherein the composition is analyzed for the presence of proteins as the molecules containing amine or thiol groups.

13. The method of claim 7 further comprising the step of subjecting the carrier to a separation technique prior to step b so as to separate any molecules containing amine or thiol groups.

14. The method of claim 13, wherein said separation technique is performed using an electric current.

15. The method of claim 13, wherein said separation technique is a chromatographic separation technique.

* * * * *

UNITED STATES PATENT AND TRADEMARK OFFICE
CERTIFICATE OF CORRECTION

PATENT NO. : 4,680,272
DATED : July 14, 1987
INVENTOR(S) : Tammy L. Smith

It is certified that error appears in the above-identified patent and that said Letters Patent is hereby corrected as shown below:

Column 1, line 64, delete "thr" and insert therefor -- the --.

Column 2, line 59, delete "light".

Column 3, line 57, delete "Dbromomaleimied" and insert therefore -- Dibromomaleimide --.

Signed and Sealed this

Twenty-fourth Day of November, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,680,272

DATED : July 14, 1987

INVENTOR(S) : TAMMY L. SMITH

It is certified that error appears in the above-identified patent and that said Letters Patent is hereby corrected as shown below:

Column 1, line 6, delete "5-R01-6M 2427" and insert therefor -- 5-R01-GM 24427 --.

Signed and Sealed this

Seventeenth Day of May, 1988

Attest:

DONALD J. QUIGG

Attesting Officer

Commissioner of Patents and Trademarks